United States Patent
Singh et al.

(10) Patent No.: US 9,395,345 B2
(45) Date of Patent: Jul. 19, 2016

(54) DUST DISCRIMINATION FOR SENSING SYSTEMS

(75) Inventors: Rajiv Kumar Singh, Glen Waverley (AU); Kemal Ajay, Mount Waverley (AU)

(73) Assignee: Xtralis Technologies Ltd (BS)

( * ) Notice: Subject to any disclaimer, the term of this patent is extended or adjusted under 35 U.S.C. 154(b) by 668 days.

(21) Appl. No.: 13/582,846

(22) PCT Filed: Mar. 3, 2011

(86) PCT No.: PCT/AU2011/000238
§ 371 (c)(1),
(2), (4) Date: Nov. 13, 2012

(87) PCT Pub. No.: WO2011/106841
PCT Pub. Date: Sep. 9, 2011

(65) Prior Publication Data
US 2013/0199270 A1     Aug. 8, 2013

(30) Foreign Application Priority Data
Mar. 5, 2010   (AU) ................................ 2010900936

(51) Int. Cl.
G01N 1/22      (2006.01)
G01N 33/00     (2006.01)
G08B 17/10     (2006.01)

(52) U.S. Cl.
CPC .......... *G01N 33/0027* (2013.01); *G01N 1/2202* (2013.01); *G08B 17/10* (2013.01)

(58) Field of Classification Search
CPC ... G01N 1/2202; G01N 33/0027; G08B 17/10
See application file for complete search history.

(56) References Cited

U.S. PATENT DOCUMENTS

| 4,223,559 A | 9/1980 | Chuan et al. |
| 4,254,414 A | 3/1981 | Street et al. |

(Continued)

FOREIGN PATENT DOCUMENTS

| CN | 1315655 | 10/2001 |
| CN | 101261225 A | 9/2008 |

(Continued)

OTHER PUBLICATIONS

"International Application No. PCT/AU2011/000238, International Search Report and Written Opinion mailed Mar. 21, 2011", (Mar. 29, 2011), 11 pgs.

(Continued)

*Primary Examiner* — Lisa Caputo
*Assistant Examiner* — Punam Roy
(74) *Attorney, Agent, or Firm* — Schwegman, Lundberg & Woessner, P.A.

(57) ABSTRACT

A sensing system and method for detecting particles in an air volume includes a main airflow path including an inlet from the air volume. Also included is a collection site within the main airflow path. The collection site is for drawing an air sample from the main airflow path. Additionally the system includes a means to induce a localized increase in particle speed at the collection site relative to air speed along the remainder of the main airflow path. The means to induce a localized increase includes an auxiliary airflow path from the main airflow path. The auxiliary airflow path has an exit upstream of the collection site. In an alternative form of the invention, the means to induce the localized increase in particle speed at the collection site comprises a venturi in the main airflow path with the collection site being disposed along the venturi.

20 Claims, 2 Drawing Sheets

(56) References Cited

U.S. PATENT DOCUMENTS

| | | | |
|---|---|---|---|
| 6,807,844 B2 * | 10/2004 | Kogure et al. | ............... 73/28.01 |
| 7,834,773 B2 | 11/2010 | Kato | |
| 2009/0237259 A1 * | 9/2009 | Yokota | ........................ 340/628 |
| 2009/0237261 A1 | 9/2009 | Yokota | |

FOREIGN PATENT DOCUMENTS

| | | |
|---|---|---|
| JP | 2009-245138 A | 10/2009 |
| TW | 200945267 | 11/2009 |
| WO | WO-2005/052288 A2 | 6/2005 |

OTHER PUBLICATIONS

Taiwan Application No. 100107372, Taiwan Search Report mailed Apr. 2015 (with English commentary), (Apr. 2015), 11 pgs.

Taiwanese Patent Application Ser. No. 100107372, Search Report completed Jan. 18, 2016, (English Translation), 1 pg.

European Application Serial No. 11750088.4, Extended European Search Report mailed Mar. 15, 2016, 8 pgs.

* cited by examiner

DUST DISCRIMINATION FOR SENSING SYSTEMS

PRIORITY CLAIM TO RELATED APPLICATIONS

This application is a national stage application under 35 U.S.C. §371 of PCT/AU2011/000238, filed Mar. 3, 2011, and published as WO 2011/106841 A1 on Sep. 9, 2011, which claims priority to Australian Application No. 2010900936, filed Mar. 5, 2010, which applications and publication are incorporated by reference as if reproduced herein and made a part hereof in their entirety, and the benefit of priority of each of which is claimed herein.

FIELD OF THE INVENTION

The present invention relates to a sensing system and method for detecting particles in an air volume. More particularly, although not exclusively, the invention relates to an aspirating smoke detector. However, the invention is not limited to this particular application and other types of sensing systems for detecting particles in an air volume are included within the scope of the present invention.

BACKGROUND OF THE INVENTION

Smoke detection systems can be falsely triggered by exposure to dust. In aspirating smoke detection systems, various analytical solutions have been implemented in order to detect the dust and thereby avoid a false alarm. In light-scatter-based smoke detection systems, dust discrimination may be implemented by using time-amplitude analysis (individual dust particles or small clouds of dust tend to produce a spike in the scatter signal) or by using multiple light wavelengths, multiple polarisations, multiple viewing angles or combinations of the above. These analytical tools add complexity to the smoke detection systems.

Another means to limit problems associated with dust is to limit the introduction of dust into the smoke detection chamber. This is achieved through various means, such as filtration or inertial separation in which smaller particles suspended in an air stream are preferentially drawn into the sample site. These smaller particles are more likely to be associated with smoke than dust. The momentum of larger and heavier particles tend to take them past the sampling port volume without being drawn into it.

By way of example, FIG. 1 illustrates the operation of a typical inertial separator. The air flow A travels within the sampling pipe D to a sampling port of sampling collection tube E. The heavier and larger particles B are carried past the sampling port of the sampling collection tube while a proportion of the smaller, lighter particles C are drawn into the sampling port and then to the sampling site for analysis. The remainder of the airflow F leaves the system.

The problem with inertial separation is that it is not effective unless there is rapid air movement in the sampling pipe D. However, this rapid air movement within the sampling pipe D is not always practical, requiring a larger fan with higher energy requirements than would otherwise be required.

It is therefore an object of the present invention to provide an improved sensing system which addresses the abovementioned disadvantage, or at least provides the public with a useful choice over known systems.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

In accordance with an aspect of the present invention, there is provided a sensing system for detecting particles in an air volume, the sensing system including:
  a main airflow path including an inlet from the air volume;
  a collection site within the main airflow path, the collection site for drawing an air sample from the main airflow path; and
  means to induce a localised increase in particle speed at the collection site relative to air speed along the remainder of the main airflow path, the means to induce a localised increase including an auxiliary airflow path from the main airflow path, the auxiliary airflow path having an exit upstream of the collection site.

The means to induce a localised increase in the particle speed at the collection site may include a means to increase air speed and/or airflow at the collection site. The auxiliary airflow path recirculates air drawn from the main airflow path. Thus air in the main air flow path, parallel to the auxiliary air flow path, thereby flows at a higher speed than the airflow along the remainder of the main airflow path. The auxiliary airflow path may include a fan to draw air into the auxiliary airflow path.

In a most preferred form of the invention, the auxiliary airflow path may be in the form of a circulating loop. Preferably, the entrance to the circulating loop is downstream from the collection site and the exit from the circulating loop is upstream from and adjacent to the collection site. In a most preferred form of the invention, the exit of the circulating loop projects into the main airflow path immediately adjacent to the collection site. The exit of the auxiliary airflow path or circulating loop may be smaller than the opening so that the exit speed of the air is greater than the speed at the opening (being drawn from the main airflow path).

The collection site suitably employs the principles of inertial separation for promoting collection of smaller particles in favour of larger particles. The collection site may comprise a sample collection tube projecting, into the main airflow path. Preferably, the sample collection tube has an outer surface that is closed at the portion which faces the upstream direction of airflow. The opening for collecting particles from the airflow is formed in the outer surface portion of the collection tube which faces downstream of the airflow.

The sensing system may include a detector to which the sample flows for testing. The detector may be in the form of a particle detector such as a light-scatter particle detector. Preferably, the particle detector is a smoke detector. Suitably, the detector can be connected to a fire alarm system and optionally, to an appropriate suppressant system.

The airflow path suitably includes a sampling pipe network including a sampling pipe and inlet ports. The sensing system preferably includes a sub-sampling path that draws air from the collection site and includes a fan, a detection chamber and optionally, a filter.

In accordance with a second aspect of the present invention, there is provided a method of sensing particles in an air volume, the method comprising:
  drawing air from the air volume and causing airflow along a main airflow path past a collection site;
  inducing a localised increase in particle speed at the collection site, relative to air speed along the remainder of the main airflow path using an auxiliary airflow path from the main airflow path, the auxiliary airflow path having an exit upstream of the collection site; and testing an air sample drawn from the collection site.

The step of inducing the localised increase in particle speed may be non-continuous and may depend on the result of a pre-testing step. The auxiliary airflow path such as a circulating loop may include a fan to create the localised increase in particle speed at the collection site. This fan may run continuously so that all of the air samples drawn from the collection site have the benefit of improved inertial separation. Alternatively, the fan may run intermittently. In one preferred method, there may be an initial pre-testing step which operates periodically or intermittently. If the pre-testing step detects a predetermined level of particulate matter then the fan is operated to induce the localised increase in particle speed and testing of the air sample is then conducted to take a reading of the air sample under the conditions more favourable to particle mass discrimination.

In accordance with a third aspect of the present invention, there is provided a sensing system for detecting particles in an air volume, the sensing system including:

a main airflow path which is substantially straight, the main airflow path including an inlet from the air volume;

a collection site in the form of a sample tube projecting into the main airflow path, the sample tube for drawing an air sample from the main airflow path; and means to induce a localised increase in particle speed at the collection site relative to air speed along the remainder of the main airflow path, the means to induce the localised increase in particle speed at the collection site comprising a venturi in the main airflow path with the collection site being disposed along the venturi.

In accordance with a fourth aspect of the present invention, there is provided a method of sensing particles in an air volume, the method comprising:

drawing air from the air volume and causing airflow along a substantially straight main airflow path past a collection site;

inducing a localised increase in particle speed at the collection site, relative to air speed along the remainder of the main airflow path, by the use of a venturi in the main airflow path, with the collection site being disposed along the venturi;

inducing a transverse airflow along a transverse flow path which is transverse to the main airflow path; and testing the transverse airflow.

In accordance with a fifth aspect of the present invention, there is provided a smoke sensing system for detecting particles in an air volume, the sensing system including:

a main airflow path including an inlet from the air volume;

a collection site for drawing an air sample from the main airflow path;

means to induce a localised increase in particle speed at the collection site relative to air speed along the remainder of the main airflow path, the means to induce the localised increase in particle speed at the collection site comprising a venturi in the main airflow path with the collection site being disposed along the venturi; and a smoke detector for testing the air sample.

In accordance with a sixth aspect of the present invention, there is provided a method of sensing smoke particles in an air volume, the method comprising:

drawing air from the air volume and causing airflow along a main airflow path past a collection site;

inducing a localised increase in particle speed at the collection site, relative to air speed along the remainder of the main airflow path, by the use of a venturi in the main airflow path with the collection site being disposed along the venturi;

inducing a sample flow away from the main airflow path; and testing the sample flow for smoke particles.

Preferably, in the third to sixth aspects recited above, the collection site is disposed at a narrow portion or the narrowest part of the venturi.

As used herein, except where the context requires otherwise, the term "comprise" and variations of the term, such as "comprising", "comprises" and "comprised", are not intended to exclude further additives, components, integers or steps.

BRIEF DESCRIPTION OF THE DRAWINGS/FIGURES

Exemplary embodiments of the present invention will now be described by way of non-limiting example only, with reference to the accompanying drawings, in which.

DETAILED DESCRIPTION OF THE EMBODIMENTS

Figure 1:
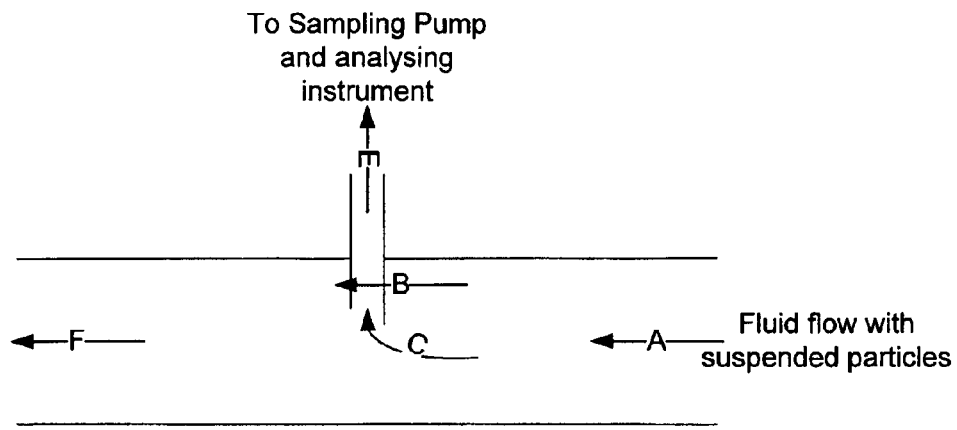
FIG. 1 illustrates a prior art arrangement of a sensing system with an inertial separator.
Figure 2:
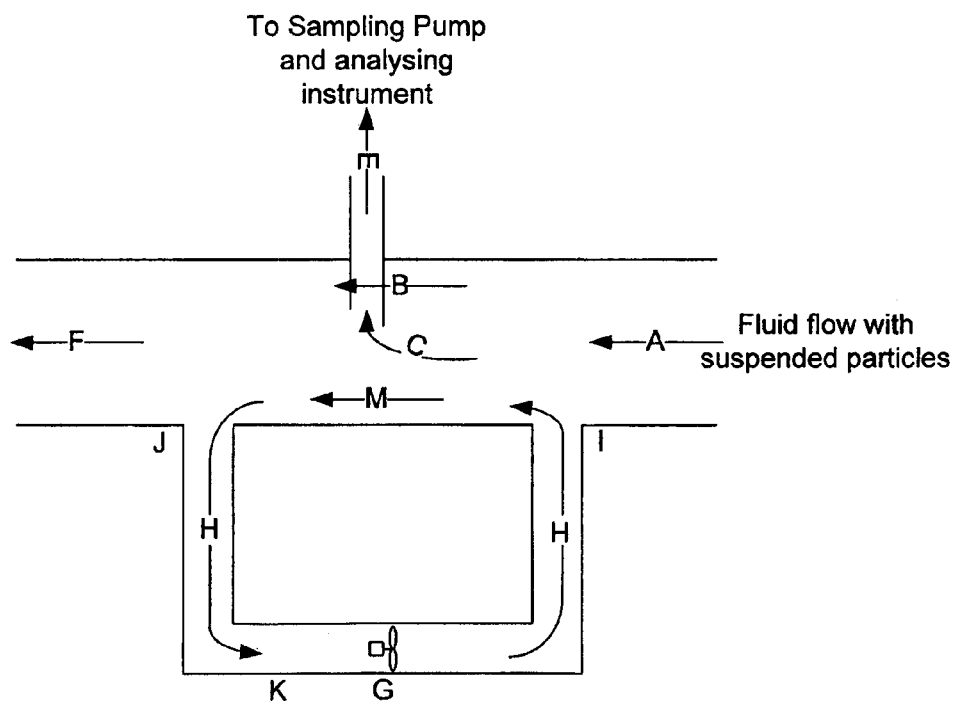
FIG. 2 illustrates a sensing system according to a preferred embodiment of the present invention.

The sensing system of FIG. 2 includes a sampling pipe D which defines the main airflow path A,F. The main airflow path A,F passes a sample collection tube E projecting into the main airflow path A,F. The sampling collection tube E has an opening which faces downstream of the main airflow path and is used to draw an air sample which then passed to a test chamber for analysis. A sub-sample of the main airflow is drawn into the sampling collection tube E and the momentum of the larger and heavier particles B tend to take them past the opening of the sample collection tube E without being drawn into the opening. The smaller, lighter particles C are drawn into the sampling collection tube E from where they are drawn away to the detector for analysis (not shown).

A circulating loop K has an entrance J downstream of the sampling collection tube E and exits at I back into the main airflow path A, upstream of the sampling collection tube E. The circulating loop K incorporates a fan G which draws airflow H through the circulating loop K. The recirculating air increases the speed of the airstream flowing through the main loop along M parallel to the circulating loop K, and past the opening of the sampling collection tube E. However, this localised increased speed of airflow in the circulating loop K has little or no, effect on the flows upstream A and downstream F of the recirculating airstream H,M.

Figure 3:
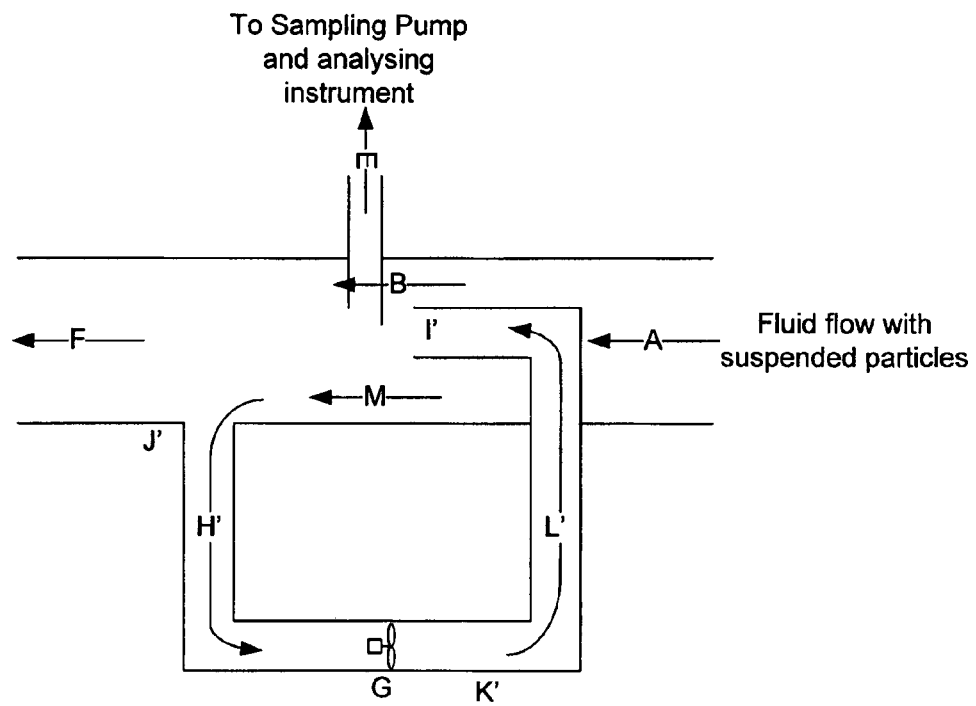
FIG. 3 illustrates an alternative embodiment of the sensing system of FIG. 2.

In FIG. 3, the use of similar or the same reference numerals as FIG. 2 illustrates like parts, the prime symbol (') indicating where a part has been modified for the new embodiment.

FIG. 3 illustrates an enhancement whereby the exit I' of the circulating loop K' projects into the main airflow path adjacent and upstream of the sampling collection tube E. The exit I' has an orifice of much smaller diameter than the downstream entrance J' to the circulating loop K'. Therefore, the exit speed of the airstream L' at the exit I' is much greater than the speed of the inlet airflow H'.

The sensing system of FIGS. 2 and 3 can be operated in at least two ways. Firstly, the duct fan G may run continuously to assist in providing ongoing separation between large and small particles. This has the advantage of ease of operation but has two drawbacks. The first is the lifespan of the fan G is reduced due to its continuous operation and exposure to background dust and smoke levels. The second drawback is that continuous operation of the fan G continuously consumes power.

Alternatively, the fan may be operated by only turning it on when some particulate is detected by the sensing system. The change in reading once the fan is operating is indicative of the relative amount of large and small particles in the airstream and thus can be used to give an indication as to whether the detected particulate is dust or smoke, or provide other indication of the nature of the particles or condition being sensed. Because the fan G is operated infrequently, it is likely to last longer. Another advantage of this arrangement is that when the fan is off it consumes no power.

Figure 4:
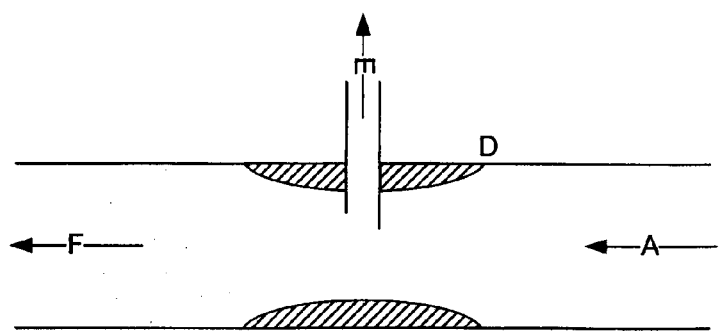
FIG. 4 illustrates a further embodiment of the sensing system.

In a third embodiment illustrated in FIG. 4, a venturi is employed in the sampling pipe D with the sampling collection tube being disposed at or adjacent the throat of the venturi where the air speed increases. This embodiment does not increase the total airflow past the sampling collection tube, but increases the local airspeed at its location, thereby increasing momentum of the particles entrained in the airflow and increasing the inertial separation effect of the sampling collection tube. This embodiment has the advantage of not adding any moving parts to the system.

The foregoing describes only one embodiment of the present invention and modifications may be made thereto without departing from the scope of the invention.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A sensing system for detecting particles in an air volume, the sensing system including:
   a particle detector;
   a main airflow path including an inlet from the air volume;
   a sample collection site within the main airflow path from which an air sample is drawn from the main airflow path for delivery to the particle detector; and
   an auxiliary airflow path drawing air from the main airflow path and having an exit into the main airflow path, at a location upstream of the sample collection site, from which air leaves the auxiliary airflow path and is introduced into the main airflow path thereby inducing a localized increase in air speed at the sample collection site relative to air speed at a point in of the main airflow path upstream of the exit.

2. The sensing system as claimed in claim 1 wherein the auxiliary airflow path includes a fan to draw air into the auxiliary airflow path.

3. The sensing system as claimed in claim 1 or claim 2 wherein the auxiliary airflow path is in the form of a circulating loop with an entrance to the circulating loop being downstream from the sample collection site and the exit from the circulating loop being upstream from the sample collection site.

4. The sensing system as claimed in claim 3 wherein the exit of the circulating loop projects into the main airflow path immediately adjacent to the sample collection site.

5. The sensing system as claimed in claim 3 wherein the exit of the auxiliary airflow path is smaller than its entrance so that the exit speed of the air is greater than the speed at its entrance.

6. A method of sensing particles in an air volume, the method comprising:

drawing air from the air volume into a main airflow path and past a sample collection site in the main airflow path;

inducing a localized increase in air speed at the sample collection site by using an auxiliary airflow path to draw air from the main airflow path, and introduce the air into the main airflow path from an exit upstream of the sample collection site, the localized increase in air speed being relative to air speed at a point in the main airflow path upstream from the exit; and testing an air sample drawn from the sample collection site.

7. The method as claimed in claim 6 wherein the auxiliary airflow path includes a fan to draw air into the auxiliary airflow path.

8. The method as claimed in claim 7 wherein the fan is run continuously.

9. The method as claimed in claim 7 wherein the fan is run intermittently.

10. The method as claimed in claim 9, further including:

pre-testing an air sample drawn from the sample collection site to determine the level of particulate matter in the sample;

determining whether the level is above a predetermined threshold;

running the fan; and testing another air sample drawn from the sample collection site.

11. A sensing system for detecting particles in an air volume, the sensing system including:

a particle detector;

a main airflow path which is substantially straight, the main airflow path including an inlet from the air volume;

a sample collection site in the form of a sample tube projecting into the main airflow path, the sample tube for drawing an air sample from the main airflow path for delivery to the particle detector; and means to induce a localized increase in air speed at the sample collection site relative to air speed along the remainder of the main airflow path, the means to induce the localized increase in particle speed at the sample collection site comprising a venturi in the main airflow path, with the sample collection site being disposed along the venturi.

12. The sensing system as claimed in claim 11 wherein the sample collection site is disposed at a narrow portion or the narrowest part of the venturi.

13. A method of sensing particles in an air volume, the method comprising:

drawing air from the air volume and causing airflow along a substantially straight main airflow path past a sample collection site;

inducing a localized increase in air speed at the sample collection site, relative to air speed along the remainder of the main airflow path, by the use of a venturi in the main airflow path, with the sample collection site being disposed along the venturi;

inducing a transverse airflow along a transverse flow path which is transverse to the main airflow path; and testing the transverse airflow.

14. The method as claimed in claim 13 wherein the sample collection site is disposed at a narrow portion or the narrowest part of the venturi.

15. A smoke sensing system for detecting particles in an air volume, the sensing system including:
- a main airflow path including an inlet from the air volume;
- a sample collection site for drawing an air sample from the main airflow path;
- means to induce a localized increase in air speed at the sample collection site relative to air speed along the remainder of the main airflow path, the means to induce the localized increase in particle speed at the sample collection site comprising a venturi in the main airflow path with the sample collection site being disposed along the venturi; and
- a smoke detector for testing the air sample.

16. The sensing system as claimed in claim 15 wherein the sample collection site is disposed at a narrow portion or the narrowest part of the venturi.

17. A method of sensing smoke particles in an air volume, the method comprising:
- drawing air from the air volume and causing airflow along a main airflow path past a sample collection site;
- inducing a localized increase in air speed at the sample collection site, relative to air speed along the remainder of the main airflow path, by the use of a venturi in the main airflow path, with the sample collection site being disposed along the venturi;
- inducing a sample flow away from the main airflow path; and
- testing the sample flow for smoke particles.

18. The method claimed in claim 17 wherein the sample collection site is disposed at a narrow portion or the narrowest part of the venturi.

19. The sensing system as claimed in claim 3 wherein the auxiliary airflow path includes a fan to draw air into the auxiliary airflow path.

20. The sensing system of claim 7 wherein the air is drawn into the auxiliary airflow path from a position downstream of the sample collection site.

* * * * *